United States Patent [19]
Haswell

[11] Patent Number: 5,916,527
[45] Date of Patent: Jun. 29, 1999

[54] CONVERTIBLE STAND AND CONTAINER AND METHOD

[75] Inventor: James S. Haswell, Olathe, Kans.

[73] Assignee: Beckwell International, Inc., Olathe, Kans.

[21] Appl. No.: 08/810,069

[22] Filed: Mar. 4, 1997

[51] Int. Cl.⁶ ..................................................... B01L 9/06
[52] U.S. Cl. ........................... 422/104; 422/99; 422/102; 436/810
[58] Field of Search ............... 422/99, 100, 102, 422/103, 104; 436/180, 810

[56] References Cited

U.S. PATENT DOCUMENTS

| | | | |
|---|---|---|---|
| 3,802,844 | 4/1974 | Sendra et al. | 422/104 |
| 4,929,427 | 5/1990 | Guala | 422/100 |
| 4,963,493 | 10/1990 | Daftsios | 435/287 |
| 5,137,693 | 8/1992 | Mawhirt | 422/104 |
| 5,186,339 | 2/1993 | Heissler | 211/74 |
| 5,217,694 | 6/1993 | Gibler et al. | 422/104 |
| 5,378,433 | 1/1995 | Duckett et al. | 422/100 |
| 5,665,309 | 9/1997 | Champsiex et al. | 422/63 |
| 5,700,429 | 12/1997 | Buhler et al. | 422/104 |

Primary Examiner—Harold Y. Pyon
Attorney, Agent, or Firm—Litman, McMahon & Brown, L.L.C.

[57] ABSTRACT

A convertible stand and container is provided for specimen tubes and includes first and second sides each having proximate and distal portions. In a stand configuration the side proximate portions are releasably latched together and the side distal portions are folded double over the outsides of the proximate portions. A plurality of receiver proximate sections are formed between the side proximate portions. In a container configuration the side distal portions are releasably attached together and form receiver distal sections therebetween which align with the receiver proximate sections to provide receivers for containing the specimen tubes.

17 Claims, 7 Drawing Sheets

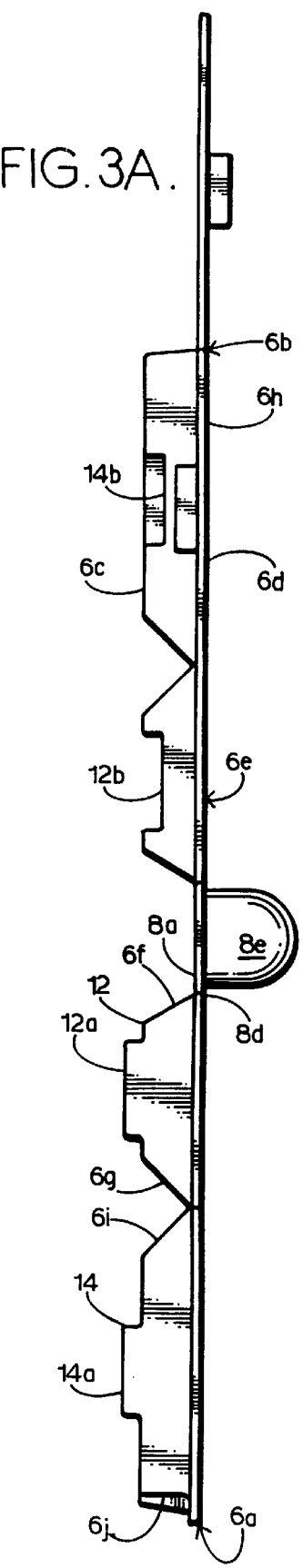

FIG. 4
FIG. 4A.
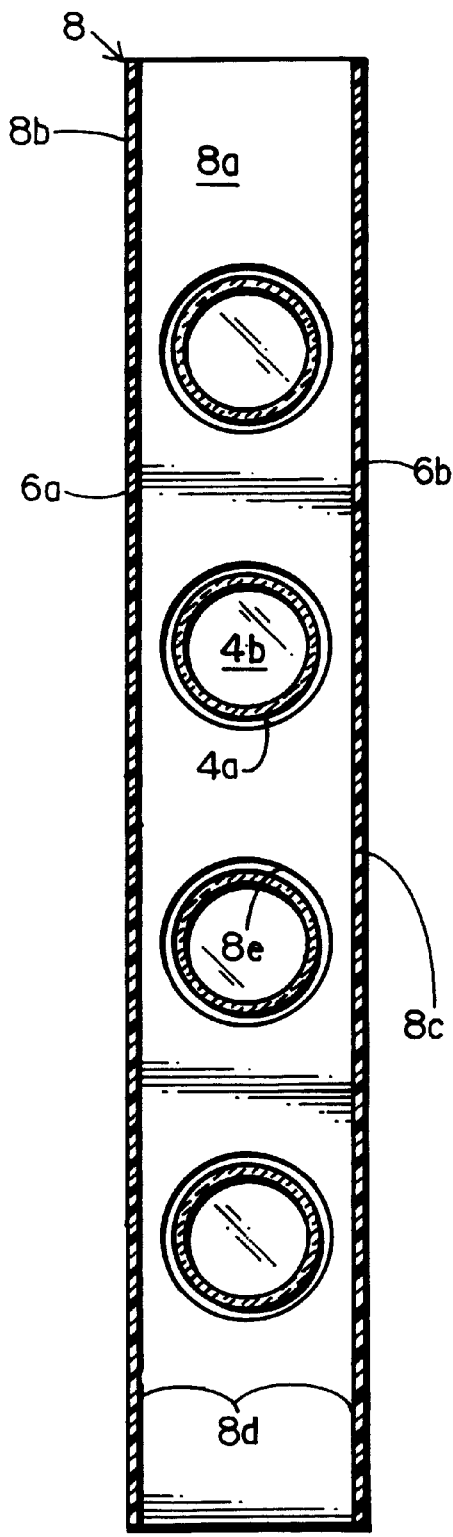
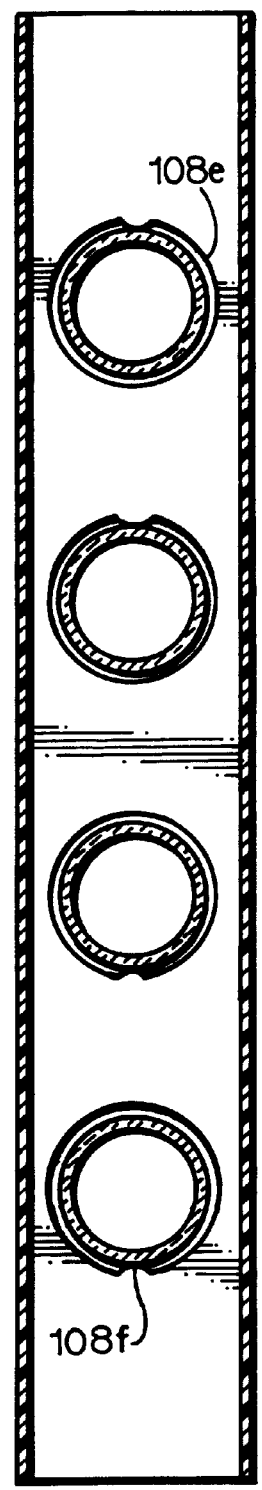

CONVERTIBLE STAND AND CONTAINER AND METHOD

BACKGROUND OF THE INVENTION

1. Field of the Invention

The present invention relates generally to stands and containers, and in particular to a convertible stand and container for medical specimen tubes.

2. Description of the Related Art

Stands, containers and other devices for receiving and enclosing objects are well known and a variety of different designs have previously been implemented to satisfy the requirements of particular applications. Containers are often designed to protect their contents, such as a mailing container which permits the mailing of breakable items.

Other devices have been proposed which function as stands for supporting objects in desired orientations. For example, vessels and receptacles for receiving fluids are often mounted in a particular orientation for convenience while transferring fluids, recording data, etc.

Medical diagnostic and testing work often involves the collection of fluid specimens from patients. For example, blood and breath tests are often performed by obtaining the necessary specimens from patients and sending them to testing laboratories for analysis. The specimens are often mailed in tubes from testing locations, such as physicians' offices, to centralized testing laboratories. Such testing specialization can reduce the costs associated with medical testing because well-equipped laboratories can analyze specimens efficiently.

However, a problem with transporting specimens is that specimen receivers, which often comprise glass vacuum tubes, are susceptible to breakage in transit. Moreover, for accurate analysis the specimen tubes must be carefully handled and identified to ensure that they are associated with the right individual and that adequate tests are performed to confirm the results of a medical procedure. For example, medical procedures are often monitored by taking "baseline" samples before treatment and post-treatment samples at a predetermined time interval after treatment to determine effectiveness.

Kits are available for taking medical samples and include specimen tubes for receiving same. Since the specimens tend to look alike, the tubes must be marked or somehow identified with such information as the patient's name, the date taken, baseline or post-treatment, etc. Therefore, there is a need for a device for identifying specimen tubes with certain pertinent data.

Still further, it is desirable to provide a device for supporting the specimen tubes in an upright orientation during the testing process. Specimen tube stands are available for this purpose, but specimen tubes placed therein would still be susceptible to misidentification when mailed. To overcome this problem considerable care is required on the part of lab technicians and medical technicians. Therefore, there is a need for a device or system which simplifies the handling of specimen tubes when the specimens are collected and when they are mailed, and also to reduce the risk of misidentification. Such a device would preferably provide a convenient receptacle or stand for the specimen tubes during the specimen collection and analysis phases and would facilitate mailing, transporting and storing the specimen tubes in a protected enclosure. A convertible device for supporting the specimen tubes during collection and analysis procedures, and for enclosing the test tubes for transport or storage, would be particularly desirable. Heretofore there has not been available such a device with the advantages and features of the present invention. The present invention addresses the shortcomings of the prior art.

SUMMARY OF THE INVENTION

In the practice of the present invention, a convertible stand and container is provided for specimen tubes. The convertible stand and container includes opposite sides each having proximate and distal portions. The side proximate portions are connected together by a bottom panel subassembly. In a stand configuration the side proximate portions are latched together in opposed relation and the side distal portions are folded double over the respective side proximate portions. A plurality of receiver proximate sections are formed between the side proximate portions and each receives a specimen tube which protrudes upwardly therefrom. In a container configuration, the side distal portions are folded into generally coplanar alignment with the side proximate portions and are releasably latched together. The side distal portions form receiver distal sections therebetween which align with respective receiver proximate sections. A flap has a base position under the bottom panel subassembly in the stand configuration and also has a retracted position releasably latched to a respective side distal portion in the container configuration.

OBJECTS AND ADVANTAGES OF THE INVENTION

The principle objects and advantages of the present invention include: providing a convertible stand and container for specimen tubes; providing such a convertible stand and container which forms upwardly-open receivers in its stand configuration; providing such a convertible stand and container which encloses the specimen tubes in its container configuration; providing such a convertible stand and container which includes a dual-purpose flap with a base position in the stand configuration and a retracted position in the container configuration, with the flap providing a mounting for an identifying label; providing such a convertible stand and container which can be formed from readily available materials utilizing existing machinery; providing such a convertible stand and container which facilitates the secure collection and transportation of fluid specimens; providing such a convertible stand and container which is adapted for mailing in its container configuration; and providing such a convertible stand and container which is economical to manufacture, efficient in operation, capable of a long operating life and particularly well adapted for the proposed uses thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 3a is a side elevational view of the convertible stand and container, shown in a generally flat configuration after a molding step in its manufacture.

FIG. 4 is a horizontal, cross-sectional view of the convertible stand and container taken generally along line 4—4 in FIG. 2.

FIG. 4a is a horizontal, cross-sectional view of the convertible stand and container, particularly showing a modified bottom subassembly with retainer ridges in receiver ends thereof.

DETAILED DESCRIPTION OF THE INVENTION

Figure 1:
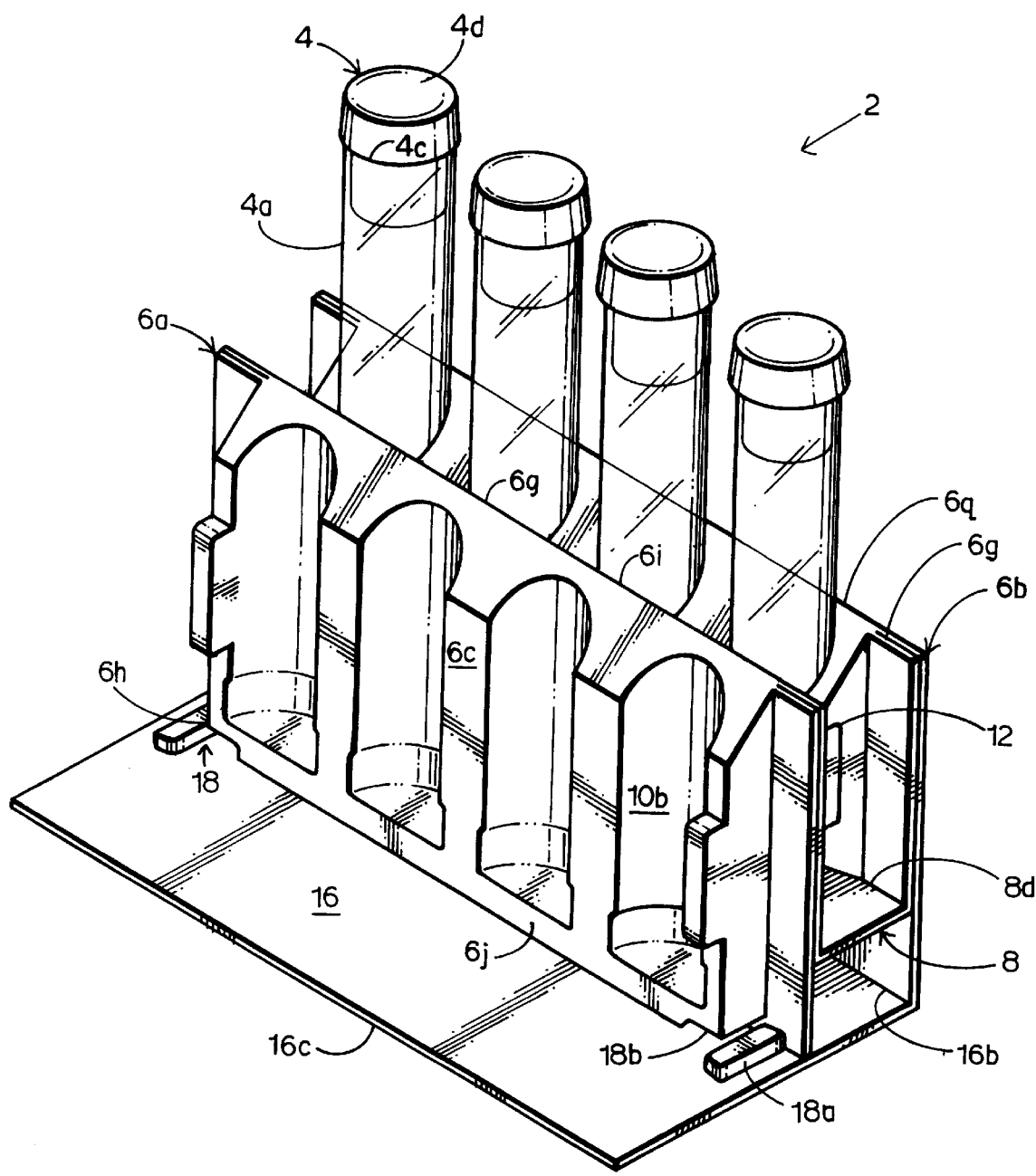
FIG. 1 is an upper, perspective view of a convertible stand and container for specimen tubes embodying the present invention, shown in a stand configuration thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

I. Introduction and Environment

Referring to the drawings in more detail, the reference numeral 2 generally designates a convertible stand and container for tubes, such as the specimen tubes 4. Without limitation on the generality of useful applications of the convertible stand and container 2, it is disclosed herein in connection with specimen tubes 4 each having a tube body 4a with a rounded, closed end 4b and a stopper end 4c receiving a rubber stopper 4d. The specimen tubes 4 can comprise, for example, the vacuum type which are commonly used for drawing patient fluid samples by piercing the stopper 4c with a needle or cannula attached to a tube for conveying body fluids from a test subject or another vessel. Such tubes are available from Becton Dickinson Systems, Rutherford, N.J. 07070 under its "VACUTAINER®" trademark, and from Sherwood Medical of St. Louis, Mo., under the trademark "MONOJECT®".

II. Convertible Stand and Container 2

The convertible stand and container 2 includes first and second sides 6a,b. In a stand configuration (FIG. 1), the sides 6a,b are folded double to provide access to the specimen tubes 4. In a container configuration (FIG. 2), the sides 6a,b are generally juxtaposed and are positioned in opposing relation to enclose and contain the specimen tubes 4.

Each side 6a,b includes a receiver face 6c and an opposite or folding face 6d. In a container configuration (FIG. 2), the receiver faces 6c form inner faces of the sides 6a,b and the opposite faces 6d form outer faces thereof. Each side 6a,b includes a proximate portion 6e with first and second edges 6f,g and a distal portion 6h with first and second edges 6i,j. The proximate portion edges 6f,g are beveled to form acute angles, as are the distal portion first edges 6i.

Each side 6a,b includes a plurality of parallel channels 6k extending generally longitudinally and open at the side receiver face 6c. Each channel 6k includes a channel proximate section 6m extending generally between and open at respective side proximate portion edges 6f,g and a channel distal section 6n extending from and open at a respective side distal portion first edge 6i and terminating in spaced relation inwardly from a respective side distal portion second edge 6j to form an enclosed receiver distal end 6p. Each side 6a,b includes a transverse side hinge line 6q which hingedly interconnects the proximate portion second edge 6g and the distal portion first edge 6i whereby the side proximate and distal portions 6e,h can hingedly fold with respect to each other between the stand and the container configurations.

A bottom panel subassembly 8 includes a bottom panel 8a with opposite margins 8b,c each hingedly connected to a respective side proximate portion first edge 6f by a respective bottom hinge line 8d for folding the sides 6a,b with respect to the bottom panel 8a. The bottom panel subassembly 8 includes a plurality (e.g., four are shown) of proximate or bottom receiver ends 8e depending downwardly from the bottom panel 8a (FIG. 4). The receiver ends 8e are upwardly-open at the bottom panel 8a and are closed downwardly. FIG. 4 shows the smooth-bore receiver ends 8e receiving the specimen tube closed ends 4b. FIG. 4a shows modified receiver ends 108e, each of which includes a ridge 108f projecting inwardly for resiliently gripping a respective specimen tube closed end 4b whereby the specimen tubes 4 are releasably captured in the receiver ends 108e and thus retained in the convertible stand and retainer 2.

In the container configuration (FIG. 2), parallel receivers 10 are formed by respective opposed pairs of channels 6k. Each receiver 10 includes a proximate section 10a formed by an opposed pair of channel proximate sections 6m and a distal section 10b formed by an opposed pair of channel distal sections 6n. Each receiver 10 also includes a respective bottom receiver end 8e formed in the bottom panel subassembly 8. In the stand configuration (FIG. 1) the receiver distal sections 10b are eliminated by separating the side distal portions 6h. Thus, in the stand configuration shown in FIG. 1, the receivers 10 include proximate sections 10a and bottom receiver ends 8e or 108e.

Side latch means are provided for selectively latching the side proximate and distal portions 6e,h together and include a plurality of proximate side latches 12 for releasably latching the side proximate portions 6e together. Each proximate side latch 12 includes a dovetail tab 12a projecting inwardly from a respective side receiver face 6c and a corresponding, opposed dovetail recess 12b formed in the receiver face 6c of the other side proximate portion 6e for selectively receiving the tab 12a.

Distal side latches 14 are provided for releasably latching the side distal portions 6h together and include dovetail tabs 14a selectively received in dovetail recesses 14b. The proximate side latches 12 are provided on both sides of each receiver proximate section 10a for a total of five proximate side latches 12 for four receivers 10. Two distal side latches 14 are provided, each located outside a respective outermost receiver distal section 10b. The side proximate portions 6e can thus be more securely latched than the side distal portions 6h to facilitate separating the side distal portions 6h (with five proximate latches 12 as opposed to two distal latches 14) when reconfiguring from the container configuration (FIG. 2) to the stand configuration (FIG. 1). In other words, pulling outwardly on the side distal portions 6h can separate them with a relatively small amount of force, which would not be sufficient to separate the side proximate portions 6e since the latter are normally intended to remain latched together by more proximate latches 12 in both the stand and container configurations.

A flap 16 includes a connected edge 16a hingedly connected to a respective side distal portion second edge 6j along a flap hinge line 16b and a flap free edge 16c. The flap 16 has a base position in the stand configuration (FIG. 1) wherein it is folded under the bottom panel subassembly 8 and is secured to the other side distal portion second edge 6j by a flap latch 18 comprising a boss 18a projecting from the flap 16 and engaging an edge recess 18b formed in the other side distal portion 6h in proximity to its second edge 6j. The other side distal portion second edge 6j thus abuts the flap 16 whereby the flap 16 is substantially perpendicular to the sides 6 and provides a base for the convertible stand and container 2 in its stand configuration with the double-folded sides 6 positioned generally upright (FIG. 1).

In the container configuration (FIG. 2), the flap 16 has a retracted position folded over the opposite face 6d of the side distal portion 6h to which the flap 16 is connected and is retained there by the flap latch bosses 18a being received in respective flap latch side recesses 18c.

Figure 2:
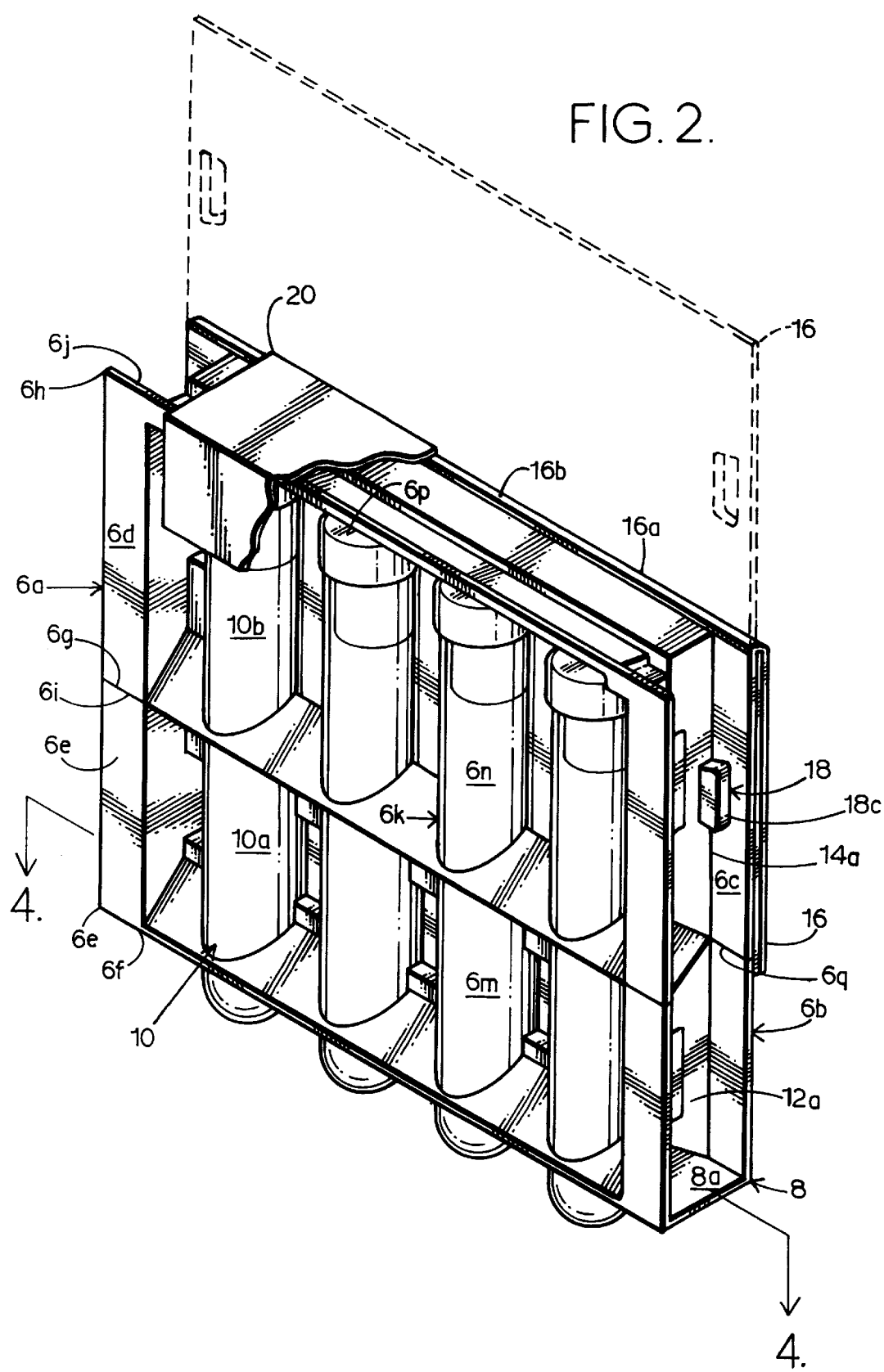
FIG. 2 is an upper, perspective view of the convertible stand and container, shown in a container configuration thereof. The dashed lines indicate an extended position of a flap.

The flap 16 is adapted to mount an identifying label/seal 20. The label and seal 20 adhesively mounts to the flap 16 and the opposite side distal portion opposite face 6d in overlying relation with respect to the side distal portion second edges 6j. A suitable adhesive can be used for securing the label/seal 20 in place in the container configuration (FIG. 2). Tube labels 22 can be applied to the tubes 4 and can be printed for identification with the label/seal 20.

III. Construction and Operation

The convertible stand and container 2 embodying the present invention can assume various alternative configurations within the scope of the present invention. For example, other numbers of receivers 10 could be provided, including a single receiver 10.

Figure 3B:
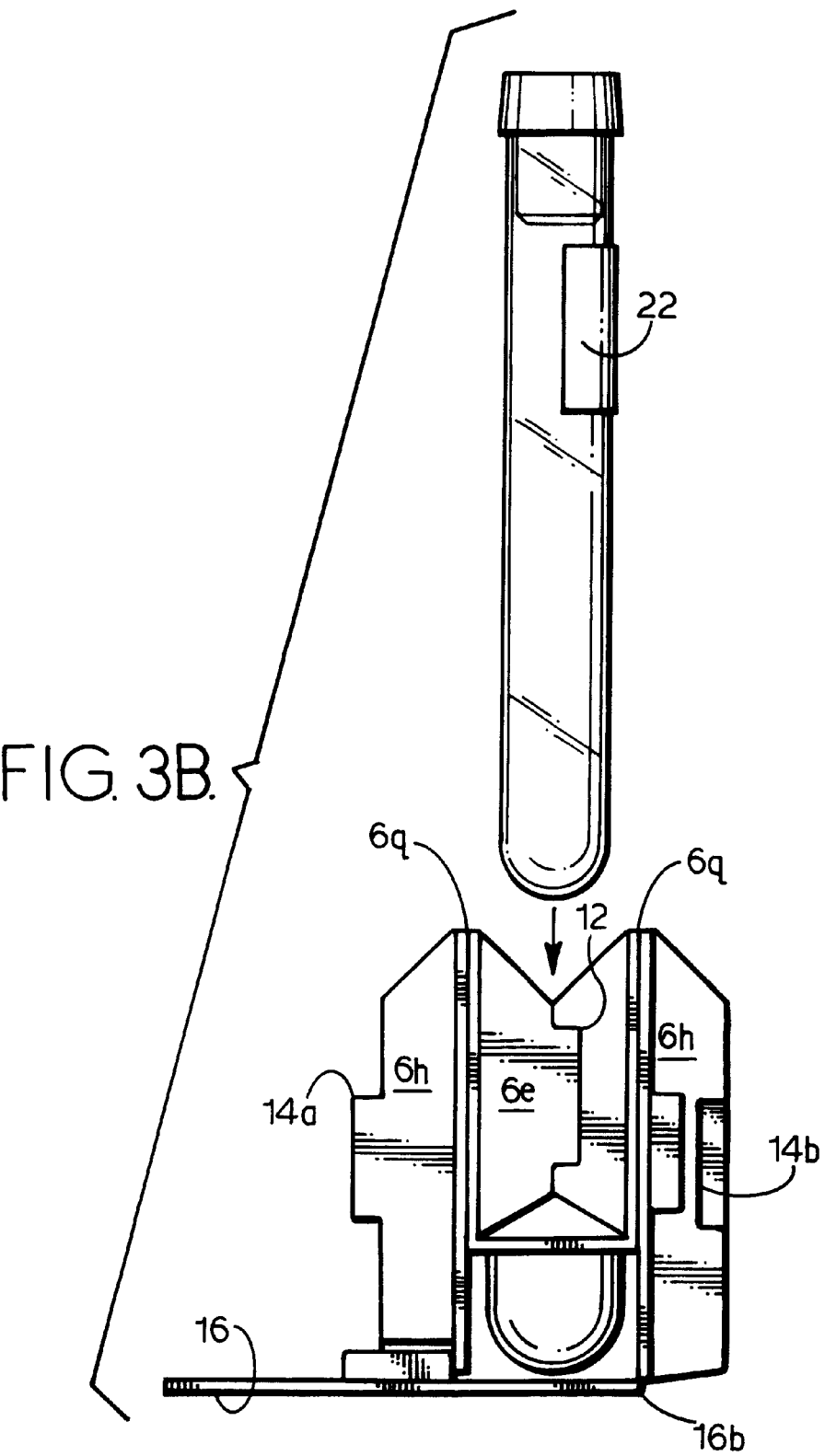
FIG. 3b is a side elevational view of the convertible stand and container, shown in its stand configuration.
Figure 3C:
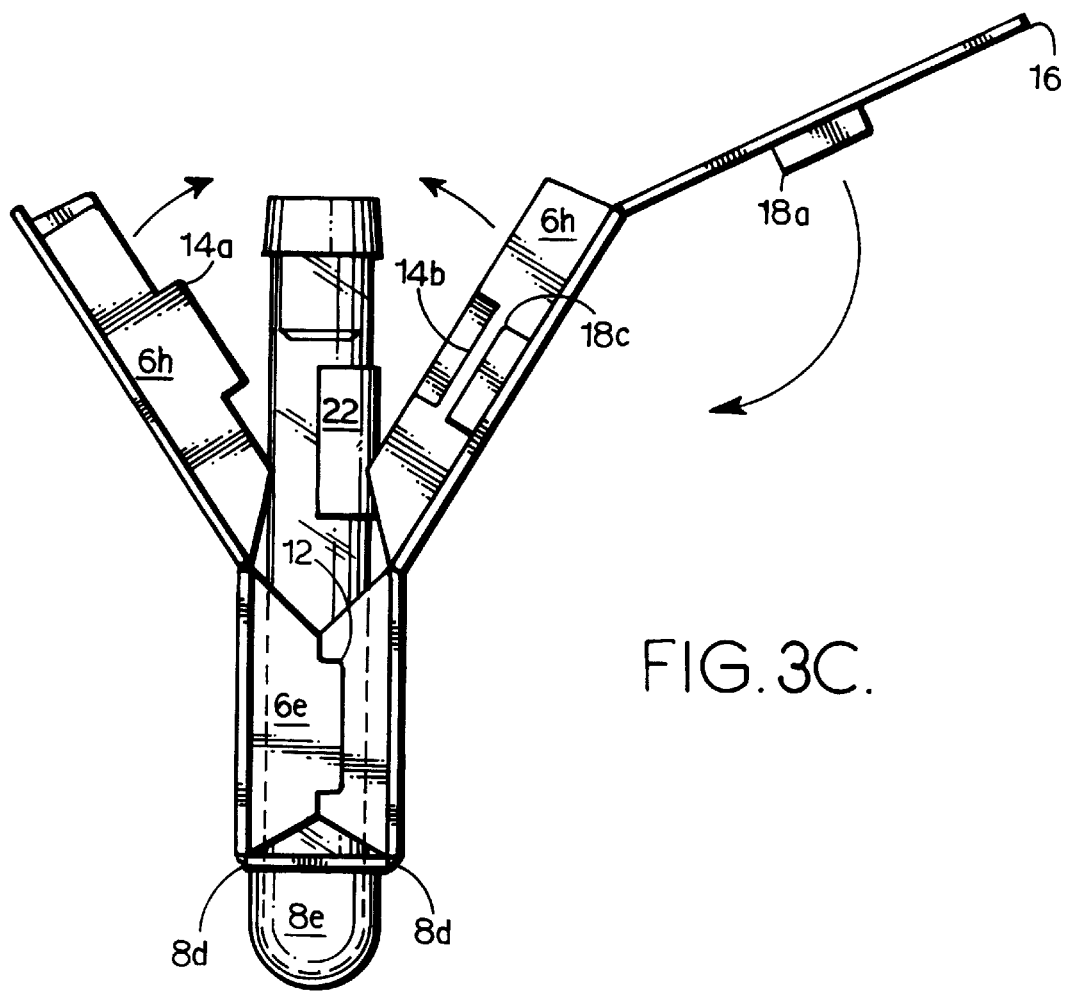
FIG. 3c is a side elevational view of the convertible stand and container, shown in an interim configuration being folded from its stand configuration to its container configuration.
Figure 3D:
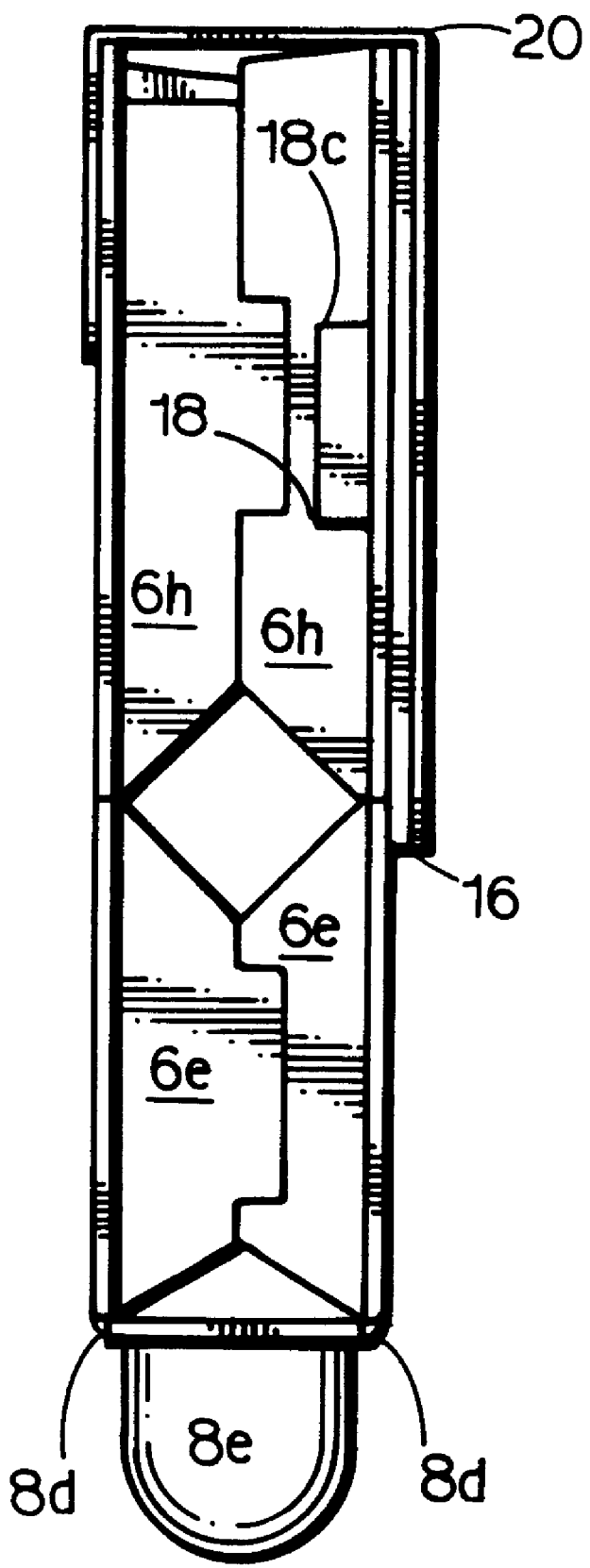
FIG. 3d is a side elevational view of the convertible stand and container, shown in its container configuration.

The convertible stand and container tube can be constructed of various materials. Clear, flexible plastics, such as polypropylene, have been found to be suitable for this purpose and can be vacuum-formed with a custom mold on conventional equipment. In the manufacturing process, the sides 6, the bottom panel subassembly 8 and the flap 16 are generally flat and coplanar (FIG. 3a). The respective hinge lines 6q, 8d and 16b accommodate folding of the vacuum-formed blank to the stand and container configurations.

In the stand configuration (FIG. 1) the receivers 10 are easily accessible for inserting specimen tubes 4 thereinto and withdrawing specimens tubes 4 therefrom. The beveled side proximate portion second edges 6g facilitate guiding the specimen tubes 4 into the receiver proximate sections 10a. The side distal portions 6h are slightly longer than the side proximate portions 6e whereby the side distal portion second edges 6j generally align with or are positioned below the bottom receiver ends 8e for abutting the flap 16 in its base position (FIG. 2).

In the container configuration (FIG. 2), the convertible stand and container 2 securely retain the specimen tubes 4 for shipment and for protecting from breakage. The label/seal 20 can be applied to the convertible stand and container 2 in its container configuration (FIG. 2) before use as a security against tampering. The label/seal would then be broken in order to reconfigure the convertible stand and container 2 to its stand configuration (FIG. 1). The tube labels 22 can include information, such as bar code indicia, numerical identifiers, etc., for matching corresponding indicia printed on the label/seal 20. The label/seal 20 and the tube label 22 can be color-coded to identify the baseline specimens and specimens taken after treatment. A label/seal such as that shown at 20, or some other suitable security seal can be applied to the convertible stand and container 2 in its container configuration (FIG. 2) for security after the samples are secured therein. The convertible stand and container 2 can be packed with an appropriate form for filling out with patient and testing information.

As an example of the use of multiple specimens, two of the specimen tubes 4 can contain baseline readings taken before treatment. The other two specimen tubes 4 can contain specimens taken a predetermined length of time after treatment, such as thirty minutes. Thus, the efficacy of treatment can be monitored by testing the baseline and the post-treatment specimens.

It is to be understood that while certain forms of the present invention have been illustrated and described herein, it is not to be limited to the specific forms or arrangement of parts described and shown.

What is claimed and desired to be secured by Letters Patent is as follows:

1. A convertible stand and container for a specimen tube, which includes:
   (a) first and second sides, each side having:
      (1) a proximate portion with first and second edges;
      (2) a distal portion with first and second edges; and
      (3) a channel with a proximate section extending along said proximate portion and a distal section extending along said distal portion;
   (b) said side proximate portions being connected together in juxtaposed relation;
   (c) first and second hinge means each hingedly interconnecting a respective side proximate portion second edge and a respective side distal portion first edge;
   (d) a closed, container configuration with said side distal portions positioned in juxtaposed relation;
   (e) an open, stand configuration with said side distal portions folded along respective hinge means over respective side proximate portions; and
   (f) said channel proximate sections forming a receiver proximate section and said channel distal sections forming a receiver distal section in said container configuration, said receiver proximate and distal sections being aligned in said container configuration and collectively forming a receiver for receiving and generally enclosing the specimen tube.

2. The invention according to claim 1, which includes:
   (a) each said side having receiver and opposite faces, said receiver faces at said side distal portions being positioned in opposed relation in said closed, container configuration; and
   (b) respective side opposite faces of said proximate and distal sections of each said side being positioned in opposed relation in said open, stand configuration with each said side being folded double.

3. The invention according to claim 2, which includes:
   (a) latch means for releasably securing said side distal portions together in said closed, container configuration.

4. The invention according to claim 3, which includes:
   (a) said latch means comprising a tab on one of said side distal portions projecting from the receiver face thereof and a recess on the other of said side distal portions open at the receiver face thereof, said tab being releasably received in said recess in said closed, container configuration.

5. The invention according to claim 1, which includes:
   (a) said latch means comprising distal latch means; and
   (b) proximate latch means for latching said side proximate portions together.

6. The invention according to claim 1, which includes:
   (a) a bottom panel extending between said side proximate portion first edges; and
   (b) said receiver having a closed end depending downwardly from said bottom panel.

7. The invention according to claim 6, which includes:
   (a) a ridge formed in said receiver closed end and projecting inwardly thereinto.

8. The invention according to claim 2, which includes:
   (a) a flap having connected and free edges;
   (b) a flap hinge connecting said flap connected edge to a respective side distal portion second edge;
   (c) said flap having a base position in said stand configuration, said flap in its base position being positioned below said side proximate portion first edges; and
   (d) said flap having a retracted position in said container configuration folded about said flap hinge and positioned over a respective side opposite face.

9. The invention according to claim 8, which includes:
   (a) flap latch means for releasably securing said flap to one of said side distal portions in its base position and for latching said flap to the other of said side distal portions in its retracted position.

10. The invention according to claim 9 wherein said flap latch means includes:
    (a) a pair of bosses projecting from said flap;
    (b) a pair of flap latch base position recesses formed in said one side distal portion and receiving said flap latch bosses with the flap in its base position; and
    (c) a pair of flap latch retracted position recesses formed in said other side distal portion and receiving said flap latch bosses with said flap in its retracted position.

11. The invention according to claim 8, which includes:
    (a) said sides extending generally perpendicularly upwardly from said flap in its base position.

12. The invention according to claim 1, which includes:
    (a) said side proximate portion second edges and said side distal portion first edges being beveled.

13. The invention according to claim 1, which includes a plurality of said receivers extending in generally parallel, spaced relation.

14. The invention according to claim 1, which includes:
    (a) a label/seal mounted on said sides over said distal portion second edges in said closed, container configuration.

15. The invention according to claim 14, which includes:
    (a) specimen identifying indicia printed on said label/seal; and
    (b) a tube label for mounting on the tube and having specimen identifying indicia printed thereon, said tube label indicia corresponding to the label/seal indicia.

16. A convertible stand and container for specimen tubes, which includes:
    (a) first and second sides each having:
       (1) a proximate portion with first and second edges;
       (2) a distal portion with first and second edges;
       (3) side hinge means for hingedly connecting said proximate portion second edge and said distal portion first edge;
       (4) a plurality of channels each having a proximate section extending between the proximate portion edges and a distal section extending from the distal portion first edge into the distal portion;
       (5) said proximate portion edges being beveled;
       (6) said distal portion first edge being beveled; and
       (7) receiver and opposite faces, said channels being open at said receiver face;
    (b) a bottom panel subassembly including a bottom panel with opposite margins each connected to a respective side proximate portion first edge along a respective bottom hinge line, said bottom panel subassembly including a plurality of closed bottom receiver ends depending downwardly from said bottom panel;
    (c) a closed, container configuration with said side distal portions positioned together;
    (d) an open, stand configuration with said side distal portions each positioned adjacent to a respective side proximate portion;
    (e) a plurality of receivers each having a respective receiver proximate section formed by an opposed pair of said channel proximate sections, a respective receiver distal section in said container configuration formed by an opposed pair of said channel distal sections, and a respective one of said receiver ends in alignment with said receiver proximate section;
    (f) a plurality of proximate side latches each including a dovetail tab extending from a respective side receiver face at a respective side proximate portion and a dovetail recess open at the receiver face of the other side proximate portion;
    (g) a plurality of distal side latches each including a dovetail tab projecting from a respective side receiver face at a respective side distal section and a dovetail recess open at the receiver face of the other side distal portion;
    (h) a flap including a connected edge hingedly connected to a respective side distal portion second edge along a flap hinge line and a free edge;
    (i) a flap base position with said convertible stand and container in its stand configuration and with said flap extending generally beneath said side proximate section first edges in generally perpendicular relation with respect to said sides;
    (j) a flap retracted position over a respective opposite face of the distal portion of the side to which the flap is connected; and
    (k) a plurality of flap latches each including:
       (1) a boss projecting from said flap;
       (2) a flap latch base position recess formed in the second edge of the other side distal portion; and
       (3) a flap latch retracted position recess formed in the opposite face of the side to which said flap is attached.

17. A method of handling a plurality of specimen tubes, which includes the steps of:
    (a) forming a stand with first and second sides;
    (b) providing each side with a proximate portion and a distal portion;
    (c) releasably latching said side proximate portions together;

(d) releasably latching each said side distal portion to a respective side proximate portion;

(e) providing a flap in a base position under said sides;

(f) forming a plurality of tube receiver proximate sections between said side proximate portions;

(g) inserting a plurality of specimen tubes into said tube receiver proximate sections;

(h) releasing said side distal portions from said side proximate portions;

(i) folding said side distal portions with respect to said side proximate portions;

(j) releasably latching said side distal portions together in generally coplanar relationship with respective side proximate portions;

(k) forming receiver distal sections between said side distal portions with said specimen tubes enclosed therein;

(l) folding said flap over a respective side distal portion; and (m) releasably latching said flap to said side distal portion.

* * * * *